United States Patent [19]

Tice et al.

[11] Patent Number: 4,897,268

[45] Date of Patent: Jan. 30, 1990

[54] DRUG DELIVERY SYSTEM AND METHOD OF MAKING THE SAME

[75] Inventors: Thomas R. Tice; Richard M. Gilley, both of Birmingham, Ala.

[73] Assignee: Southern Research Institute, Birmingham, Ala.

[21] Appl. No.: 81,289

[22] Filed: Aug. 3, 1987

[51] Int. Cl.$^4$ ............................................. A61F 5/46
[52] U.S. Cl. .................... 424/422; 424/426; 424/455; 424/486; 424/488; 424/489
[58] Field of Search ................. 424/426, 78, 497, 489, 424/486, 488, 422, 455; 514/800

[56] References Cited

U.S. PATENT DOCUMENTS

| | | | |
|---|---|---|---|
| 3,737,337 | 6/1973 | Schnoring et al. | 117/100 |
| 3,773,919 | 11/1973 | Boswell et al. | 424/78 |
| 3,824,227 | 7/1974 | Rees et al. | 260/112.5 |
| 3,826,796 | 7/1974 | Sarantakis et al. | 260/112.5 |
| 3,835,108 | 9/1974 | Immer et al. | 260/112.5 |
| 3,853,837 | 12/1974 | Fujino et al. | 424/177 |
| 3,887,699 | 6/1975 | Yolles | 424/19 |
| 3,892,723 | 7/1975 | McKinley et al. | 260/112.5 |
| 3,896,105 | 7/1975 | Chai et al. | 260/112.5 |
| 3,972,859 | 8/1976 | Fujino et al. | 424/177 |
| 3,991,766 | 11/1976 | Schmitt et al. | 128/335.5 |
| 4,003,846 | 1/1977 | Kuhn et al. | 252/316 |
| 4,008,209 | 2/1977 | Fujino et al. | 424/177 |
| 4,010,125 | 3/1977 | Schally et al. | 260/8 |
| 4,010,196 | 3/1977 | Tsuk | 260/484 |
| 4,011,312 | 3/1977 | Reuter et al. | 424/78 |
| 4,033,938 | 7/1977 | Augurt et al. | 260/78.3 R |
| 4,066,568 | 1/1978 | Nakazawa et al. | 252/316 |
| 4,076,798 | 2/1978 | Casey et al. | 424/24 |
| 4,093,709 | 6/1978 | Choi et al. | 424/19 |
| 4,107,071 | 8/1978 | Bayless | 252/316 |
| 4,118,470 | 10/1978 | Casey et al. | 424/19 |
| 4,131,648 | 12/1978 | Choi et al. | 424/19 |
| 4,145,410 | 3/1979 | Sears | 424/19 |
| 4,148,871 | 4/1979 | Pitt et al. | 414/19 |
| 4,166,800 | 9/1979 | Fong | 252/316 |
| 4,180,646 | 12/1979 | Choi et al. | 528/153 |
| 4,211,769 | 7/1980 | Okada et al. | 424/177 |
| 4,234,571 | 11/1980 | Nestor et al. | 424/177 |
| 4,293,539 | 10/1981 | Ludwig et al. | 424/19 |
| 4,318,905 | 3/1982 | Nestor et al. | 424/177 |
| 4,341,767 | 7/1982 | Nestor et al. | 424/177 |
| 4,439,199 | 3/1984 | Amkraut et al. | 604/894 |
| 4,490,291 | 12/1984 | Fujino | 424/177 |
| 4,568,559 | 2/1986 | Nuwayser et al. | 424/497 |
| 4,622,244 | 11/1986 | Lapka et al. | 424/497 |
| 4,675,189 | 6/1987 | Kent et al. | 424/426 |
| 4,760,053 | 7/1988 | Labrie | 514/800 |
| 4,767,628 | 8/1988 | Hutchinson | 424/426 |
| 4,775,660 | 10/1988 | Labrie et al. | 514/800 |

FOREIGN PATENT DOCUMENTS

| | | |
|---|---|---|
| 11756565 | 10/1984 | Canada. |
| 0052510 | 11/1981 | European Pat. Off.. |
| 0058481 | 1/1982 | European Pat. Off.. |
| 0202065 | 5/1986 | European Pat. Off.. |
| 2051580 | 3/1971 | Fed. Rep. of Germany. |
| 615662 | 2/1980 | France. |
| 718150 | 7/1971 | South Africa. |
| 1332505 | 10/1973 | United Kingdom. |
| 2026976 | 2/1980 | United Kingdom. |
| 2034182 | 6/1980 | United Kingdom. |
| 8706129 | 10/1987 | World Int. Prop. O.. |

OTHER PUBLICATIONS

Sanders et al., *Journal of Pharmaceutical Sciences*, vol. 73, pp. 1294–1296, Sep. 1984.

(List continued on next page.)

*Primary Examiner*—Ellis P. Robinson
*Assistant Examiner*—P. L. Prater
*Attorney, Agent, or Firm*—Needle & Rosenberg

[57] ABSTRACT

A compatible, biodegradable microcapsule delivery system for active ingredients, including hormonally active peptides, proteins, or other bioactive molecules, and a method of making the same. The ingredients are encapsulated in biodegradable copolymer excipients of varying mole ratios and the blend of the microcapsules are administered to an animal. Delivery of the ingredient occurs over a prolonged period of time at a constant rate as a result of the varying break-down rates of the copolymer excipients.

32 Claims, 1 Drawing Sheet

OTHER PUBLICATIONS

Redding et al., *Proc. Nat'l Acad. Sci U.S.A.*, vol. 81, pp. 5845–5848, Sep. 1984.

Speiser, "Microencapsulation by Coacervation, Spray Encapsulation, and Nanoencapsulation," In *Microencapsulation*, J. R. Nixon (ed.) Marcel Dekker (1976).

Sanders et al., "Controlled Delivery of an LHRH Analogue from Biodegradable Injectable Microspheres," *J. Controlled Release* 2: 187 (1985).

Redding et al., "Long-Acting Delivery Systems for Peptides: Inhibition of Rat Prostate Tumors by Controlled Release of [D-trp$^6$] Luteinizing Hormone-Releasing Hormone from Injectable Microcapsules," *Proc. Nat'l Acad. Sci. (U.S.A.)* 81: 5845 (1984).

Sanders et al., "An Injectable Biodegradable Controlled Release Delivery System for Nafarelin Acetate," in *LHRH and its Analogues*, Labrie, Belanger and Dupont (eds.) pp. 53–62. (1984).

Kent et al., "Microencapsulation of the Peptide Nafarelin Acetate for Controlled Release," in *Long-Acting Contraceptive Delivery Systems, Program for Applied Research on Fertility Regulation Series*, pp. 169–179 (1983).

Schally, "Current Status of Antagonistic Analogs of LH-RH as a Contraceptive Method in the Female," *Research Frontiers in Fertility Regulation* (5): 1 (Jul. 1983).

Mason et al., "Hydrolytic Degradation of Poly-DL-(-Lactide)," *Polym. Sci. Technol.* 14: 279 (1981).

Beck et al., "Biodegradable Microsphere Contraceptive System," Paper Presented at the 4th Int'l Meeting on Fertility Control, Genova, Italy (Mar. 6–8, 1980).

Beck et al., "Long-Acting Steroidal Contraceptive Systems," *Research Frontiers in Fertility Regulation (Northwestern University* 1: 1 (Jul. 1980).

Lewis et al., "Sustained Release of Antibiotics from Biodegradable Microcapsules," *7th Int'l Symp. on Controlled Release of Bioactive Materials*, Ft. Lauderdale, Fla. (Jul. 28–30, 1980).

Beck et al., "New Long-Acting Injectable Microcapsule Contraceptive System," *Am. J. Obstet. Gyn.* pp. 419–426 (Oct. 1, 1979).

Beck et al., "A New Long-Acting Injectable Microcapsule System for the Administration of Progesterone," *Fert. and Steril.* 31(5): 545 (1979).

Chang, "Biodegradable Semipermeable Microcapsules Containing Enzymes, Hormones, Vaccines, and other Biologicals," *J. Bioeng.* 1: 25 (1976).

Yolles et al., "Long Acting Delivery Systems for Narcotic Antagonists II: Release Rate of Naltrexone from Poly(Lactic Acid) Composites," *J. Pharm. Sci.* 64 (2): 348 (1975).

Sanders et al., "Prolonged Controlled-Release of Nafarelin, Luteinizing Hormone-Releasing Hormone Analogue, from Biodegradable Polymeric Implants: Influence of Composition and Molecular Weight of Polymer," *J. Pharm. Sci.* 75(4): 356 (1986).

Vickery, "Comparisons of the Potential Utility of LHRH Agonists and Antagonists for Fertility Control," *J. Steroid Biochem.* 23: 779 (1985).

Schally et al., "Inhibition of Prostate Tumors by Agonistic and Antagonistic Analogs of LH-RH," *The Prostate* 4: 545 (1983).

Langer, "Controlled Release of Macromolecules," *Chemtech* pp. 98–105, (Feb. 1982).

Privalova et al., "Macrokinetics of Degradation of Polyglycolide Threads in Aqueous Solutions of Electrolytes," *Polymer Sci. U.S.S.R.)* 22(8): 2074 (1980).

Pitt et al., "Biodegradable Drug Delivery Systems Based on Aliphatic Polyesters: Application to Contraceptives and Narcotic Antagonists," *Naltrexone: Research Monogram* 28 (1980).

Wise et al., "Long Term Controlled Delivery of Levonorgestrel in Rats by Means of Small Biodegradable Cylinders," *J. Pharm. Pharmac.* 32: 399 (1980).

Benagiano et al., "Biodegradable Systems for the Sustained Release of Fertility-Regulating Agents," *J. Steroid Biochem.* 11: 449 (1979).

Gliding et al., "Biodegradable Polymers for Use in Surgery-Polyglycolic/Poly(Actic Acid) Homo- and Copolymers: I," *Polymer* 20: 1459 (1979).

Moiseev et al., "The Specificity of Polymer Degradation in the Living Body," *J. Polymer Sci: Polymer Symposium 66*, pp. 269 (1979).

Pitt et al., "Sustained Drug Delivery Systems II: Factors Affecting Release Rates from Poly($\epsilon$-Caprolactone) and Related Biodegradable Polyesters," *J. Pharm. Sci.* 68(12): 1534 (1979).

(List continued on next page.)

OTHER PUBLICATIONS

Pitt et al., "Sustained Drug Delivery Systems I: The Permeability of Poly($\epsilon$-Caprolactone), Poly(DL-Lactic acid), and their Copolymers," *J. Biomed. Mater. Res.* 13: 497–507 (1979).

Wise et al., "Lactic/Glycolic Acid Polymers," in *Drug Carriers in Biology and Medicine,* Gregoriadis (ed.), Academic Press (1979).

Krishnan et al., "Controlled Release of Bioactive Compounds with Special Reference to Agriculture," *Popular Plastics* Apr. (1978).

Wise et al., "Results on Biodegradable Cylindrical Subdermal Implants for Fertility Control," *Midland Macromolecular Monogram* (Polymer Delivery Systems) (1978).

Wise et al., "Sustained Release of Sulphadiazine," *J. Pharm. Pharmac.* 30: 686 (1978).

Wise et al., "Sustained Delivery of a Narcotic Antagonist From Lactic/Glycolic Acid Copolymer Implants," in *Polymeric Delivery Systems,* Kostelnik (ed.), Gordon & Breach Science Publishers (1978).

Miller et al., "Degradation Rates of Oral Resorbable Implants (Polylactates and Polyglycolates): Rate Modification with changes in PLA/PGA Copolymer Ratios," *J. Biomed. Mater. Res.* 11: 711 (1977).

Nelson et al., "Evaluation and Comparisons of Biodegradable Substances as Osteogenic Agents," *Oral Surg., Oral Med., Oral Path.* 43(6): 836 (1977).

Schindler et al., "Biodegradable Polymers for Sustained Drug Delivery," in *Contemporary Topics in Polymer Science,* vol. 2, Parce and Schaefgen (eds), Plenum Publishing Corp. (1977).

Anderson et al., "An Injectable Sustained Release Fertility Control System," *Contraception* 13(3): 375 (1976).

Yolles et al., "Controlled Release of Biologically Active Drugs," *Bulletin of the Parenteral Drug Ass'n* vol. 30 Nov.-Dec. (1976).

Cutright et al., "Single Dose, Long Duration, Subcutaneous Drug Administration," *J. Oral Medicine* 30(1): 5 (1975).

Nash et al., "Assessment of the Toxicity of Delivery Systems for Injectable Contraceptives," *J. Steroid Biochem.* 6: 909 (1975).

Nilsson et al., "Biodegradable Polylactate as a Steroid-Releasing Polymer: Intrauterine Administrations of d-Norgestrel," *Am. J. Obstet. Gynecol.* 122(1): 90 (1975).

Schwope et al., "Lactic/Glycolic Acid Polymers as Narcotic Antagonist Delivery Systems," *Life Sciences* 17: 1877 (1975).

Cutright et al., "Degradation Rates of Polymers and Copolymers of Polylactic and Polyglycolic Acids," *Oral Surgery* 37(1): 142 (1974).

Brady et al., "Resorption Rate, Route of Elimination, and Ultrastructure of the Implant Site of Polylactic Acid in the Abdominal Wall of the Rat," *J. Biomed. Mater. Res.* 7: 155 (1973).

Jackanicz et al., "Polylactic Acid as a Biodegradable Carrier for Contraceptive Steroids." *Contraception* 8(3): 227 (1973).

Sinclair, "Slow-Release Pesticide System Polymers of Lactic and Glycolic Acids as Ecologically Beneficial, Cost-Effective Encapsulating Materials," *Environ. Sci. & Tech.* 7(10): 955 (1973).

Hegyeli, "Use of Organ Cultures to Evaluate Biodegradation of Polymer Implant Materials," *J. Biomed. Mater. Res.* 7: 205 (1973).

Kulkarni et al., "Biodegradable Poly(Lactic Acid) Polymers," *J. Biomed. Mater. Res.* 5: 169 (1971).

Luzzi, "Microencapsulation," *J. Pharm. Sci.* 59(10): 1367 (1970).

Wiley, "Microencapsulation," in *Encyclopedia of Chemical Technology,* vol. 13, 2d ed., pp. 436–456, New York, (1967).

Ezan et al., "Radioimmunoassay of [D-Trp$^6$]-Luteinizing Hormone-Releasing Hormone: Its Application to Animal Pharmacokinetic Studies after Single Injection and Long-Acting Formulation Administration," *Regulatory Peptides* 14: 155 (1986).

Schwope et al., "Development of Polylactic/Glycolic Acid Delivery Systems for Use in Treatment of Narcotic Addiction," *Nat'l Inst. Drug Abuse Monogr. Ser.* pp. 13–18, Jan. 1976.

Thies, "Development of Injectable Microcapsules for Use in the Treatment of Narcotic Addiction," *Nat'l Inst. Drug Abuse Monogr. Ser.* pp. 19–20, Jan. 1976.

Mason et al., "Hydrolytic Degradation of Poly Dl-(-Lactide)," *Org. Coat. Plast. Chem.* 42:436 (1980).

Sanders, L. M. et al.; *J. Pharm. Sci.*, 75: 356–360 (Apr. 1986).

Schally, A. V. et al.; *Proc. Nat'l Acad. Sci., U.S.A.* 83 8764–8768 (Nov. 1986).

(List continued on next page.)

OTHER PUBLICATIONS

Tice, T. R. et al.; 11th International Symp. on Controlled Release of Bioactive Materials Ft. Lauderdale, Fla. (Jul. 1984).

Schally, A. V. et al.; Proc. Nat'l Acad. Sci. U.S.A. 82: 2498-2502 (Apr. 1985).

Mason-Garcia, M. et al.; Proc. Nat'l Acad. Sci. U.S.A., 82: 1547-1551 (Mar. 1985).

Torres-Aleman, I. et al.; Proc. Nat'l Acad. Sci. U.S.A., 82: 1252-1256 (Feb. 1985).

Asch, R. H. et al.; J. Andrology, 6: 83-88 (1985).

Sanders, L. M. et al.; 10th International Syposium on Controlled Release of Bioactive Materials, San Francisco, Calif., 91-96 (Jul. 1983).

Kent, J. S. et al.; in: Long-Acting Contraceptive Delivery Systems, Program for Applied Research on Fertility Regulation Series on Fertility Regulation, pp. 169-179 (1984).

Vickery, B. H. et al.; in: Long-Acting Contraceptive Delivery Systems, Program for Applied Research on Fertility Regulation Series on Fertility Regulation, pp. 180-189 (1984).

Kent, J. S. et al.; Reproductive Health Care International Symposium, Maui, Hawaii (Oct. 1982).

Sanders, et al.; Reproductive Health Care International Symposium, Maui, Hawaii (Oct. 1982).

Rojas, F. J. et al.; Abstract for the American Fertility Society Annual Meeting, Sep. 27-Oct. 2, 1985.

DRUG DELIVERY SYSTEM AND METHOD OF MAKING THE SAME

BACKGROUND OF THE INVENTION

It is known that a marked inhibition of pituitary and gonadal function that occurs after chronic administration of the [D-Trp[6], des-Gly[10]]-LHRH ethylamide an analog of luteinizing hormone releasing hormone (LHRH) and other LHRH analogs leads to a reduction in steroidal sex hormones and makes possible approaches for the use as a contraceptive or for the treatment of sex hormone-dependent tumors. Concerning the latter, studies involving rats treated with LHRH analogs show the potential clinical efficacy of the hormone in the treatment of prostate carcinoma and other hormone-dependent tumors in animals.

The treatment of hormone-dependent tumors and other disorders in animals would be greatly enhanced by a delivery system which, after a single administration, maintained controlled levels of active ingredients, including [D-Trp[6], des-Gly[10]]-LHRH ethylamide and its related analogs, over extended periods of time. Traditional methods of administering peptides (or proteins) result in high initial concentrations of peptide (or protein) analog in the tissue, but over a short period of time, i.e., over a few minutes to several hours, peptide levels in the blood decline. Therefore, optimal pharmacological effects are most often not achieved. The result is a need for more frequent administration of higher-dosage regimens.

More recently, a polymer of poly(D,L-lactide-co-glycolide) (DL-PLG), which is biodegradable and biocompatible with living tissue, has been used in microcapsules for longer acting delivery systems. Systems of microencapsulated active ingredients in polymers and copolymers of lactic acid and glycolic acid have been used to achieve controlled release of chemical and biological pharmaceuticals. For example, U. S. Pat. No. 3,773,919 discloses a drug, stated to include water-soluble antibiotic peptides encapsulated in lactide/glycolide copolymers so as to provide controlled release. Canadian Patent No. 1,176,565 discloses a microcapsule composition comprising a core containing a LHRH peptide encapsulated in a biodegradable, biocompatible copolymer excipient.

Microencapsulation for controlled release of enzymes, hormones and other biologicals are discussed in papers by Sanders, Kent, McRae, Vickery, Tice, and Lewis, *Journal of Pharmaceutical Sciences*, Vol. 73, pp. 1294–1296, September 1984 and by Redding, Schally, Tice and Meyers, Proc. *Natl. Acad. Sci. USA*, Vol. 81, pp. 5845–5848, September 1984. The first paper describes a system controlled by diffusion and erosion, wherein the kinetics of compound release determined by the parameters of the copolymer, and more particularly, the controlled release of nafarelin acetate, an analog of LHRH, from poly(D,L-lactide-co-glycolide) microspheres. The second paper discloses the inhibition of rat prostate tumors by controlled release of [D-Trp[6]] luteinizing hormone-releasing hormone from injectable microcapsules.

The microcapsule systems described in the above publications all share a common feature in that the release of the compound is controlled by the porosity and/or erosion of a polymer continuum. Also, all the described microcapsule systems utilize only a single type of copolymer. Therefore, while a controlled release of the compound is achieved, such is limited by the specific lactide/glycolide ratio used in the encapsulating material. At the most, the methods previously used, and particularly the peptide microcapsules, provided release times of approximately one month.

There exists, therefore, a need for a method of delivering active ingredients, including peptides, proteins and other bioactive molecules used in treating disease, which utilize the advantages of microencapsulation, but which provides a longer controlled duration of release than that presently known. Also, there exists a need for a method of providing a constant dose regimen of active ingredient throughout the longer release time provided by using biodegradable microcapsules.

SUMMARY OF THE INVENTION

This invention relates to a method of delivering an active ingredient into the system of an animal at a constant rate over a long period of time, i.e., one and one-half to six months or longer. A composition comprising a blend of free flowing spherical particles is obtained by individually microencapsulating quantities of the ingredient in different copolymer excipients which biodegrade at varying rates. An effective amount of the microcapsule blend may be administered to the animal parenterally (e.g., intravenously, intramuscularly, subcutaneously, intranasally, intraperitoneally, or by inhalation).

A quantity of these particles are of such a copolymer excipient that the core active ingredient is released quickly after injection, and thereby delivers the ingredient for an initial period. A second quantity of the particles are of such type excipient that delivery of the encapsulated ingredient begins as the first quantity's delivery begins to decline. A third quantity of ingredient may be encapsulated with a still different excipient which results in delivery beginning as the delivery of the second quantity beings to decline. Obviously, still greater assortments of excipients can be used to obtain more prolonged release time of the encapsulated ingredient. A further modification of the present invention could be to have different ingredients encapsulated within a blend of varying excipient formulations.

It is shown, therefore, that as the usefulness of one type of particle begins to decline or run out, another type begins to take over. This provides a preselected, constant rate of delivery over a prolonged period of time. For example, by varying the lactide/glycolide ratio in a poly(D,L-lactide-co-glycolide) encapsulation, as well as the types and quantities of encapsulated active ingredient, it is possible to design a long-term, controlled-release profile of choice.

More particularly, the invention relates to a compatible, biodegradable, injectable microcapsule delivery system for the peptide agonist [D-Trp[6], des-Gly[10]]-LHRH ethylamide (hereinafter referred to as the "agonist") and for the peptide antagonist [D-N-Ac-4-Cl-Phe[2], D-trp[6], D-Ala[10]]-LHRH (or an LHRH antagonist of similar structure) (hereinafter referred to as the "antagonist"). The microcapsule formation consists of free-flowing spherical particles, preferably of poly(D,L-lactide-co-glycolide) which can be administered parenterally, (e.g. intravenously, intramuscularly, subcutaneously, intranasally, intraperitoneally or by inhalation). By utilizing a combination of various polymers with different lactide/glycolide ratios, one can greatly prolong the release profile of the encapsulated LHRH analog. Delivery periods of six months or more can be achieved.

It is an object of this invention to provide a biocompatible, biodegradable microcapsule delivery system for an active ingredient which will deliver the ingredient at a constant rate over a long period of time.

It is a still further objective of this invention to provide a formulation comprising a core of active ingredient and various encapsulating copolymer excipients which is biocompatible and biodegradable and which can be utilized in a microcapsule delivery system.

It is another object of the invention to provide a biocompatible microcapsule delivery system for the agonist [D-Trp$^6$, des-Gly$^{10}$]-LHRH ethylamide which delivers the agonist at a constant rate of approximately 50 μg to 250 μg or more per day for a duration of from one and one-half to six months or more in men and women.

It is another object of this invention to provide a biocompatible, biodegradable microcapsule delivery system for the antagonist [D-N-Ac-4-Cl-Phe$^2$, D-Trp$^6$, D-Ala$^{10}$]-LHRH, or an LHRH antagonist of similar structure, which delivers that antagonist at a constant rate of about 200 μg to 500 μg or more per day for a duration of from one to three months or more.

BRIEF DESCRIPTION OF THE DRAWINGS

The microcapsule delivery system of this invention is designed to deliver an ingredient at a constant rate over time.

DETAILED DESCRIPTION OF THE INVENTION

Figure 1:
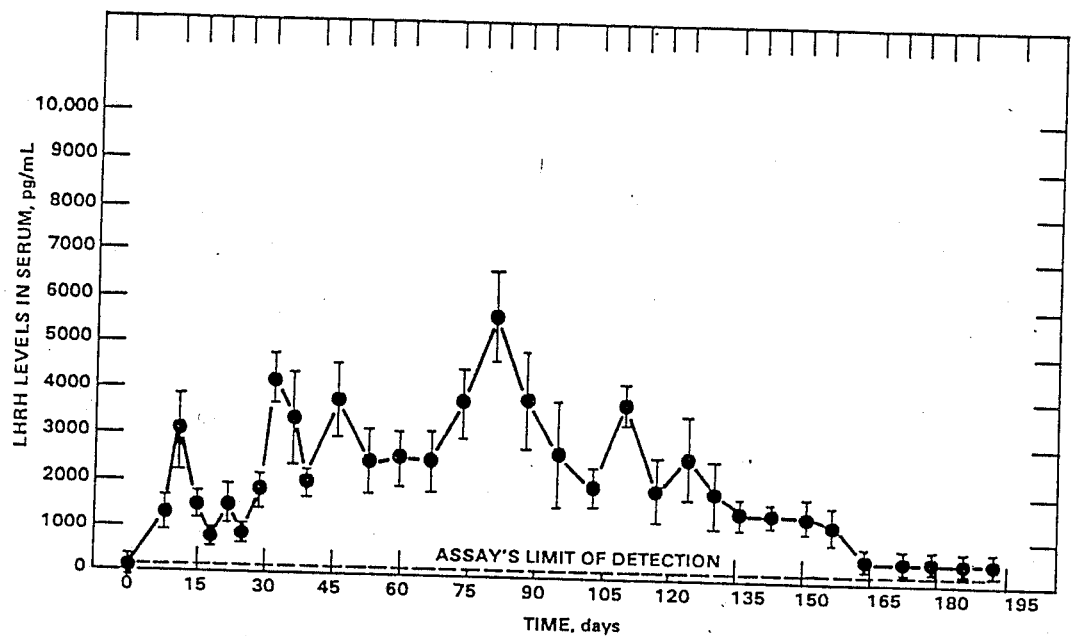
FIG. 1 shows the presence of LHRH in the blood over time. The LHRH was delivered by this invention.

An illustration of the method of performing one embodiment of the invention, that is, the use of LHRH agonist encapsulated in poly(D,L-lactide-co-glycolide), follows. In addition, the details and results of a study utilizing this embodiment in rats are provided.

It should be noted, however, that other polymers besides poly(D,L-lactide-co-glycolide) may be used. Examples of such polymers include, but are not limited to: polyacetal polymers, polyorthoesters, polyesteramides, polycaprolactone and copolymers thereof, polycarbonates, polyhydroxybuterate and copolymers thereof, polymaleamides, copolyaxalates and polysaccharides.

I. PREPARATION OF DL-PLG EXCIPIENTS

The general procedures used to prepare DL-PLG copolymers and the results of their characterization are detailed in the following sections.

a. DL-Lactide Purification

DL-lactide was used to prepare the polymers. To purify the monomer, it is first dissolved by heating a mixture of the monomer in a volume of dry (stored over molecular sieves) ethyl acetate about equal to its weight. While still hot, the solution is vacuum filtered through an extra coarse, fitted-glass gas-dispersion tube. The solvent level is reduced with an aspirator to a level equal to about half the weight of the lactide. The solution is then allowed to cool slowly to room temperature and chilled in an ice-water bath to effect crystallization. The monomer is finally filtered in a nitrogen-filled glove box. The monomer is recrystallized from ethyl acetate two additional times in this manner. All glassware used after the initial hot filtration and recrystallization is oven dried overnight at 150° C. prior to use. After the final recrystallization, the purified monomer is vacuum dried in a desiccator and stored in oven-dried glass jars until ready for use.

b. Glycolide Synthesis and Purification

The glycolide monomer is prepared and purified by the following method: Excess water is first distilled from 67% aqueous glycolic acid (Eastman Chemicals, Rochester, N.Y.) in a 3-neck flask equipped with a thermometer, distillation head, and a condenser. The solution is boiled at reduced pressure with the use of a water aspirator. After the excess water has evolved, heating is continued to remove additional water by dehydration of the glycolic acid. After no further water is evolved, the flask is allowed to cool to room temperature under vacuum. At this point, about 1 percent by weight of antimony oxide, based on the theoretical glycolic acid content, is added to the flask as a catalyst. The distillation head and condenser are removed, and the flask is connected to two receiving flasks and a trap arranged in series. The receiving flasks and trap are cooled by dry-ice:isopropanol baths. (Note: The first receiving flask is for product collection. The second receiving flask is actually a trap). The pressure is reduced to about 2 mmHg, and the reaction flask is heated to distill the crude glycolide. The material that distills between 110° and 130° C. is collected in the first receiving flask.

The crude glycolide collected is next purified by first washing the product. This is achieved by slurrying the glycolide in isopropanol, followed by filtering and vacuum drying, and then by three recrystallizations from ethyl acetate. After washing, precautions are made to protect the glycolide from atmospheric moisture during each stage of recrystallization by using oven-dried glassware, dry ethyl acetate (stored over molecular sieves), and a glove box filled with nitrogen. The crude glycolide is combined with a volume of ethyl acetate approximately equal to three-fourths its weight. The mixture is then heated to reflux to dissolve the glycolide and cooled slowly to room temperature to allow crystallization. The monomer is recrystallized three times in this manner. After each recrystallization, the glycolide crystals are collected by vacuum filtration in a glove box. After the final recrystallization, the product is dried at room temperature under a vacuum of <2 mmHg in a desiccator. The purified dried monomer is then stored in oven-dried glass jars placed inside a desiccator.

c. Copolymer Synthesis

All glassware is oven dried at 150° C. overnight and allowed to cool in a nitrogen-filled glove box. All handling of the reactants and assembling of apparatus is done in the glove box. The purified monomers are weighed directly into a 3-neck, round-bottom flask. After being charged and sealed, the flask assembly is evacuated three times, back filled with nitrogen, removed from the glove box, connected to a dry nitrogen purge, and placed into an oil bath maintained at 170° C. Once the monomers have partially melted, stirring is begun. Positive nitrogen pressure is maintained over the monomers throughout the polymerization. After the monomers have completely melted, 0.05 percent by weight of stannous octoate is introduced into the flask with a microsyringe. Stirring is continued until the mixture becomes too viscous to stir, at which point the stirrer is raised out of the melt. The polymerization is then continued for a total reaction time to 16 to 18 h. Next, the resulting polymer is allowed to cool to room temperature under a nitrogen atmosphere and removed by breaking the flask. Any residual glass is removed from the polymer plug by submerging it into liquid nitrogen. While cold, the polymer is broken into several smaller pieces and dissolved in methylene chloride and precipitated into methanol. The solvent is then removed by evaporation at room temperature under a hood and, finally, under vacuum at <2 mmHg and about 40° C. The yields are typically about 75% of theoretical. The polymers are then characterized and stored in a desiccator until ready for use.

II. PREPARATION AND CHARACTERIZATION OF AGONIST LHRH MICROCAPSULES

The phase-separation microencapsulation process is used in this example to prepare microcapsules with the LHRH agonist and DL-PLG excipients. DL-PLG is dissolved in methylene chloride and placed in a resin kettle equipped with a true-bore stirrer that is fitted with a 1.5-in. Teflon turbine impeller and powered by a Fisher Stedi-speed stirrer at a speed of about 3000 rpm. The peptide is then dispersed in the stirred copolymer solution followed by the addition of silicone oil (Dow 200 Fluid, 350 cSt, Dow Corning Corp., Midland, Mich.) to the resin kettle. This silicone oil causes the DL-PLG to coacervate and deposit onto the peptide particles. Immediately after the silicone addition is complete, the contents of the resin kettle are poured into 2 L of heptane being stirred at about 800 rpm with a 2-in. stainless steel impeller. The heptane causes the microcapsules to harden by extracting methylene chloride out of the microcapsules. After the stirring is continued for 30 min., the hard microcapsules are isolated by filtration and dried for 24 hours in a vacuum desiccator maintained at room temperature.

The core loading of the microcapsules is a measure of the amount of LHRH incorporated inside the microcapsules. This analysis is based on the extraction of core material (LHRH) from a known amount of microcapsules and quantification of the extracted LHRH by high performance liquid chromatography. A known amount of microcapsules is dissolved in methylene chloride. The LHRH is then extracted into triethylammonium phosphate (TEAP) buffer (pH 2.5) and is injected into an HPLC for quantification.

The theoretical core loading for a batch of microcapsules is based upon the copolymer and LHRH input and is calculated in the following manner:

$$\text{Theoretical Core Loading, wt \%} = \frac{\text{peptide input, } g}{(\text{copolymer input, } g) + (\text{peptide input, } g)} \times 100$$

The actual core loading is determined by assaying the microcapsules by the procedure described above. The actual core loading is calculated in the following manner:

$$\text{Actual Core Loading, wt \%} = \frac{\text{peptide assayed, } g}{\text{amt of microcapsules used in assay, } g} \times 100$$

The encapsulation efficiency is the ratio of the actual and theoretical core loadings and is calculated in the following manner:

$$\text{Encapsulation Efficiency, \% of theoretical} = \frac{\text{Actual core loading, wt \%}}{\text{Theoretical core loading, wt \%}} \times 100$$

III. PHARMACOKINETICS STUDIES OF AGONIST MICROCAPSULES IN RATS

Pharmacokinetics studies were performed involving the microencapsulation of agonist LHRH in DL-PLGs with varying lactide/glycolide ratios. A formulation of a blend of agonist microcapsules prepared with mole ratios of 52:48, 68:32, and 85:15 DL-PLG excipients were used. This blend consisted of appropriate amounts of 3%-loaded agonist microcapsules prepared with 52:48 DL-PLG, 10%-loaded against microcapsules prepared with 68:32 DL-PLG, and 8% loaded agonist microcapsules prepared with 85:15 DL-PLG excipients. The 52:48 DL-PLG component of the blend was designed to deliver agonist during the first month after administration of the microcapsules. The 68:32 DL-PLG component was designed to release the agonist primarily during the second month after administration, and the 85:15 component was designed to release the agonist primarily during the third through sixth months. Overall, the blend was designed to release approximately 50 µg of agonist per day for 180 days.

Studies with the agonist microcapsules were initiated. A total of 80 male rats were used in the studies. Three groups of 20 rats each were administered three agonist microcapsule formulations, and one group of 20 rats (a control group) was administered placebo microcapsules (empty microcapsules). Blood was collected for six months from the animals receiving the prototype six-month formulation, the 85:15 formulation, and the placebo microcapsules. Blood was collected for four months from animals treated with the agonist microcapsule formulation prepared with 68:32 DL-PLG. Ten rats from each group were bled on Fridays. Agonist serum levels were determined for all 80 rats during month 1. Thereafter, agonist serum levels were determined only for rats bled on Fridays.

CONCLUSION

The levels of agonist serum were determined using radioimmunoassay (RIA). RIA results from serum samples collected during the test period showed that a constant release of agonist LHRH was released over the six months. Correspondingly, the concentration of testosterone in serum was found to be suppressed to castrate levels during the controlled release of the LHRH from the single injection of similar microcapsules. After approximately six months, when the microcapsules were depleted of their LHRH, the testosterone levels returned to normal.

Table 1 and FIG. 1 show the agonist serum levels obtained with the prototype six-month agonist microcapsule formulation.

Table 2 shows the agonist serum levels obtained with agonist microcapsules prepared with 85:15 DL-PLG.

Table 3 shows the agonist serum levels obtained with agonist microcapsules prepared with 68:32 DL-PLG.

Table 4 shows the results of the control group study using placebo microcapsules.

TABLE 1

AGONIST SERUM LEVELS OBTAINED WITH PROTOTYPE SIX-MONTH AGONIST MICROCAPSULE FORMULATION: COMPOSITE D196-150S

| Group | Serum collection date | Day | Rat 1 | Rat 2 | Rat 3 | Rat 4 | Rat 5 | Rat 6 | Rat 7 | Rat 8 | Rat 9 | Rat 10 | Average LHRN in serum, pg/mL ± SE | |
|---|---|---|---|---|---|---|---|---|---|---|---|---|---|---|
| A | 6-24-85 | 0 | 99 | 118 | 99 | 99 | 99 | 99 | 99 | 99 | 99 | 99 | 101 | 3.4 |
| B | 6-24-85 | 0 | 99 | 100 | 99 | 100 | 99 | 100 | 100 | 100 | 99 | 99 | 100 | 0.5 |
| A | 7-02-85 | 8 | 1513 | 2555 | 1604 | 972 | 1127 | 1240 | 617 | 995 | 746 | 2050 | 1342 | 470.9 |
| B | 7-05-85 | 11 | 2133 | 2141 | 2423 | 1813 | 5416 | 3174 | 3569 | 3673 | 3602 | 3791 | 3174 | 836.8 |
| A | 7-09-85 | 15 | 1543 | 1549 | 1495 | 1777 | 1751 | 1310 | 823 | 1624 | 893 | 2013 | 1478 | 281.5 |
| B | 7-12-85 | 18 | 548 | 839 | 985 | 706 | 516 | 989 | 655 | 761 | 790 | 687 | 748 | 125.2 |
| A | 7-16-85 | 22 | 2016 | 1007 | 1503 | 2334 | 1880 | 1033 | 1101 | 1492 | 1085 | 2130 | 1558 | 425.5 |
| B | 7-19-85 | 25 | 750 | 653 | 774 | 721 | 796 | 1112 | 638 | 703 | 804 | 988 | 794 | 104.9 |
| A | 7-23-85 | 29 | 1658 | 2181 | 1723 | 1257 | 2657 | 1481 | 1937 | 2269 | 1866 | 1432 | 1846 | 335.9 |
| B | 7-26-85 | 32 | 3322 | 3701 | 5424 | 3871 | 4996 | 4254 | 4008 | 4885 | 3643 | 4493 | 4260 | 551.8 |
| A | 7-30-85 | 36 | 3893 | 5228 | 3050 | 2805 | 3909 | 2088 | 2356 | 5228 | 3898 | 1546 | 3400 | 1031.1 |
| B | 8-02-85 | 39 | 1961 | 1727 | 1637 | 2415 | 1710 | 1899 | 1750 | 2683 | 1902 | 2340 | 2002 | 286.2 |
| B | 8-09-85 | 46 | 5444 | 2921 | 4212 | 4534 | 3838 | 5008 | 2859 | 3827 | 2455 | 3044 | 3814 | 795.6 |
| B | 8-16-85 | 53 | 3340 | 1454 | 2104 | 2264 | 1433 | 3077 | 2486 | 4589 | 1834 | 2464 | 2505 | 698.5 |
| B | 8-23-85 | 60 | 2083 | 2847 | 2150 | 2181 | 2639 | 3243 | 2777 | 4544 | 2135 | 1631 | 2623 | 587.0 |
| B | 8-30-85 | 67 | 3319 | 1975 | 2023 | 1883 | 2384 | 2741 | 3680 | 2124 | 3889 | 1851 | 2587 | 656.3 |
| B | 9-06-85 | 74 | 5017 | 2471 | 3628 | 4588 | 2318 | 4639 | 4207 | 3940 | 4563 | 3223 | 3859 | 759.5 |
| B | 9-13-85 | 81 | 5206 | 5084 | 5114 | 5857 | 3154 | 7253 | 6765 | 5303 | 7314 | 6163 | 5721 | 949.1 |
| B | 9-20-85 | 88 | 4356 | 6119 | 4397 | 5007 | 2793 | 3831 | 2482 | 2485 | 4796 | 2552 | 3882 | 1053.2 |
| B | 9-27-85 | 95 | 4997 | 1856 | 2425 | 2022 | 1220 | 5916 | 2742 | 3095 | 2271 | 1227 | 2777 | 1135.3 |
| B | 10-04-85 | 102 | 2055 | 1407 | 1907 | 1864 | 1234 | 3311 | 2083 | 2805 | 2284 | 1844 | 2079 | 433.1 |
| B | 10-11-85 | 109 | 4381 | 4034 | 3959 | 4257 | 2227 | 3597 | 3960 | 4381 | 4381 | 3697 | 3887 | 428.2 |
| B | 10-18-85 | 116 | 3182 | 1206 | 1697 | 1409 | 823 | ND[b] | 2349 | 1648 | 3283 | 2382 | 1998 | 700.3 |
| B | 10-25-85 | 123 | 3878 | 1962 | 3592 | 1592 | 1402 | ND | 2340 | 2344 | 3402 | 4060 | 2730 | 871.7 |
| B | 11-01-85 | 130 | 2851 | 1399 | 2026 | 1368 | 982 | ND | 1275 | 2204 | 3662 | 1819 | 1954 | 654.7 |
| B | 11-08-85 | 137 | 1230 | 1194 | 2320 | 1326 | 1222 | ND | 1602 | 2015 | 1712 | 1041 | 1518 | 346.7 |
| B | 11-15-85 | 144 | 1463 | 933 | 1966 | 1184 | 1416 | ND | 1440 | 1889 | 1503 | 1394 | 1465 | 206.4 |
| B | 11-22-85 | 151 | 910 | 872 | 2343 | 1270 | 1560 | ND | 1355 | 2497 | 1571 | 1058 | 1493 | 441.3 |
| B | 11-29-85 | 158 | 554 | 906 | 1447 | 1015 | 1626 | ND | 1040 | 2623 | 1465 | 842 | 1280 | 463.5 |
| B | 12-06-85 | 164 | 295 | 350 | 677 | 510 | 411 | ND | 427 | 834 | 636 | 384 | 503 | 145.7 |
| B | 12-13-85 | 171 | 259 | 378 | 492 | 519 | 391 | ND | 569 | 882 | 459 | 343 | 477 | 127.1 |
| B | 12-20-85 | 178 | 275 | 533 | 755 | 442 | 392 | ND | 437 | 532 | 511 | 269 | 461 | 106.1 |
| B | 12-27-85 | 185 | 227 | 349 | 599 | 640 | 590 | ND | 355 | 610 | 518 | 324 | 468 | 134.6 |
| B | 1-03-86 | 192 | 155 | 382 | 654 | 513 | 548 | ND | 466 | 783 | 515 | 360 | 486 | 128.2 |

[a] Serum samples were analyzed at Research Triangle Institute using radioimmunoassay.
[b] ND = Not determined.

TABLE 2

AGONIST SERUM LEVELS OBTAINED WITH AGONIST MICROCAPSULES PREPARED WITH 85:15 DL-PLG: COMPOSITE D196-060-1S

| Group | Serum collection date | Day | Rat 1 | Rat 2 | Rat 3 | Rat 4 | Rat 5 | Rat 6 | Rat 7 | Rat 8 | Rat 9 | Rat 10 | Average LHRN in serum, pg/mL ± SE | |
|---|---|---|---|---|---|---|---|---|---|---|---|---|---|---|
| C | 6-24-85 | 0 | 100 | 100 | 99 | 100 | 100 | 99 | 100 | 99 | 99 | 100 | 100 | 0.5 |
| D | 6-24-85 | 0 | 100 | 99 | 913 | 100 | 130 | 100 | 99 | 124 | 115 | 99 | 188 | 145.0 |
| C | 7-02-85 | 8 | 491 | 1075 | 950 | 509 | 1097 | 1278 | 1259 | 1077 | 1061 | 1652 | 1045 | 237.1 |
| D | 7-05-85 | 11 | 2806 | 2613 | 2921 | 1465 | 1973 | 2390 | 2352 | 3434 | 3357 | 1489 | 2480 | 546.2 |
| C | 7-09-85 | 15 | 642 | 783 | 778 | 1961 | 973 | 966 | 610 | 1215 | 730 | 704 | 936 | 274.0 |
| D | 7-12-85 | 18 | 488 | 426 | 248 | 582 | 384 | 314 | 453 | 402 | 506 | 425 | 423 | 68.6 |
| C | 7-16-85 | 22 | 1417 | 460 | 609 | 1451 | 354 | 521 | 800 | 1118 | 543 | 539 | 781 | 332.2 |
| D | 7-19-85 | 25 | 441 | 346 | 315 | 491 | 770 | 191 | 480 | 508 | 471 | 477 | 449 | 100.6 |
| C | 7-23-85 | 29 | 932 | 449 | 432 | 581 | 274 | 357 | 414 | 345 | 262 | 256 | 430 | 134.6 |
| D | 7-26-85 | 32 | 384 | 467 | 964 | 1098 | 510 | 360 | 842 | 773 | 1202 | 573 | 717 | 258.5 |
| C | 7-30-85 | 36 | 1291 | 772 | 513 | 426 | 351 | 553 | 461 | 312 | 398 | 356 | 543 | 197.2 |
| D | 8-02-85 | 39 | 343 | 227 | 298 | 417 | 265 | 252 | 347 | 293 | 342 | 296 | 308 | 43.4 |
| D | 8-09-85 | 46 | 979 | 908 | 568 | 1119 | 825 | 262 | 1366 | 895 | 1586 | 1053 | 956 | 264.5 |
| D | 8-16-85 | 53 | 1679 | 1301 | 1817 | 1368 | 617 | 941 | 1332 | 1492 | 1697 | 1831 | 1408 | 295.7 |
| D | 8-23-85 | 60 | 2197 | 1981 | 1173 | 525 | 1945 | 1590 | 1993 | 2513 | 3116 | 1650 | 1868 | 507.0 |
| D | 8-30-85 | 67 | 2232 | 2449 | 2004 | 1319 | 1132 | 2196 | 1760 | 3635 | 2088 | 2029 | 2084 | 435.6 |
| D | 9-06-85 | 74 | 5206 | 4433 | 2616 | 2882 | 1381 | 4311 | 3492 | 3676 | 2115 | 1953 | 3207 | 1017.1 |
| D | 9-13-85 | 81 | 4187 | 3238 | 3742 | 3627 | 3559 | 6394 | 2302 | 3977 | 3383 | 3500 | 3791 | 637.1 |
| D | 9-20-85 | 88 | 2365 | 3549 | 2272 | 2310 | 5396 | 5202 | 2834 | 1874 | 4697 | 2708 | 3321 | 1112.2 |
| D | 9-27-85 | 95 | 3494 | 2938 | 1466 | 1812 | 1439 | 1411 | 1662 | 1142 | 2149 | 1414 | 1893 | 580.6 |
| D | 10-04-85 | 102 | 2911 | 4381 | 3878 | 2230 | 2094 | 1938 | 3168 | 1677 | 3461 | 1841 | 2758 | 801.9 |
| D | 10-11-85 | 109 | 3639 | 4381 | 4286 | 4381 | 4381 | 2745 | 4381 | 4381 | 4381 | 3222 | 4018 | 489.5 |
| D | 10-18-85 | 116 | 1323 | 2065 | 1684 | 1235 | 1080 | 886 | 1296 | 1747 | 1309 | 1080 | 1371 | 276.9 |
| D | 10-25-85 | 123 | 3781 | 2712 | 2323 | 1875 | 2400 | 1625 | 7735 | 2672 | 1408 | 3132 | 2966 | 1149.8 |
| D | 11-01-85 | 130 | 1620 | 1937 | 1819 | 1720 | 1577 | 1078 | 4031 | 3498 | 1559 | 2285 | 2112 | 695.4 |
| D | 11-08-85 | 137 | 1588 | 1244 | 1695 | 2511 | 1168 | 1199 | 3514 | 3094 | 1893 | 1340 | 1925 | 669.0 |
| D | 11-15-85 | 144 | 1736 | 1450 | 1874 | 1080 | 1297 | 804 | 5439 | 2497 | 1756 | 2111 | 2004 | 806.8 |
| D | 11-22-85 | 151 | 2638 | 1279 | 1760 | 1720 | 1319 | 1124 | 3521 | 2566 | 1418 | 1502 | 1885 | 614.2 |
| D | 11-29-85 | 158 | 1645 | 1301 | 1777 | 1119 | 1048 | 670 | 4319 | 1800 | 1174 | 1396 | 1625 | 608.3 |
| D | 12-06-85 | 164 | 748 | 680 | 780 | 533 | 724 | 396 | 970 | 580 | 784 | 525 | 672 | 130.8 |
| D | 12-13-85 | 171 | 715 | ND[b] | 816 | 740 | 699 | 349 | 1227 | 925 | 757 | 708 | 771 | 136.3 |

TABLE 2-continued

AGONIST SERUM LEVELS OBTAINED WITH AGONIST MICROCAPSULES PREPARED WITH 85:15 DL-PLG: COMPOSITE D196-060-1S

| Group | Serum collection date | Day | Rat 1 | Rat 2 | Rat 3 | Rat 4 | Rat 5 | Rat 6 | Rat 7 | Rat 8 | Rat 9 | Rat 10 | Average LHRN in serum, pg/mL ± SE | |
|---|---|---|---|---|---|---|---|---|---|---|---|---|---|---|
| D | 12-20-85 | 178 | 605 | ND | 555 | 395 | 488 | 241 | 807 | 604 | 514 | 584 | 533 | 105.4 |
| D | 12-27-85 | 185 | 572 | ND | 594 | 364 | 422 | 260 | 832 | 543 | 605 | 513 | 523 | 115.9 |
| D | 1-03-86 | 192 | 521 | ND | 666 | 514 | 660 | 314 | 1029 | 636 | 811 | 492 | 627 | 140.7 |

[a] Serum samples were analyzed at Research Triangle Institute using radioimmunoassay.
[b] ND = Not determined.

TABLE 3

AGONIST SERUM LEVELS OBTAINED WITH AGONIST MICROCAPSULES PREPARED WITH 68:32 DL-PLG: COMPOSITE D196-059-1S

| Group | Serum collection date | Day | Rat 1 | Rat 2 | Rat 3 | Rat 4 | Rat 5 | Rat 6 | Rat 7 | Rat 8 | Rat 9 | Rat 10 | Average LHRN in serum, pg/mL ± SE | |
|---|---|---|---|---|---|---|---|---|---|---|---|---|---|---|
| E | 6-24-85 | 0 | 99 | 632 | 100 | 100 | 100 | 126 | 102 | 100 | 100 | 99 | 156 | 95.2 |
| F | 6-24-85 | 0 | 100 | 99 | 99 | 99 | 158 | 100 | 100 | 100 | 89 | 100 | 104 | 10.7 |
| E | 7-02-85 | 8 | 336 | 242 | 307 | 340 | 343 | 152 | 195 | 242 | 286 | 272 | 272 | 51.0 |
| F | 7-05-85 | 11 | 435 | 287 | 519 | 390 | 285 | 480 | 370 | 423 | 389 | ND | 398 | 59.3 |
| E | 7-09-85 | 15 | 578 | 262 | 182 | 287 | 356 | 522 | 276 | 183 | 565 | 333 | 354 | 120.7 |
| F | 7-12-85 | 18 | 380 | 206 | 201 | 230 | 224 | 268 | ND[b] | 197 | 248 | ND | 244 | 40.8 |
| E | 7-16-85 | 22 | 665 | 661 | 554 | 557 | 514 | 559 | 1100 | 307 | 976 | 521 | 641 | 167.3 |
| F | 7-19-85 | 25 | 147 | 217 | 257 | 172 | 175 | 218 | ND | 310 | 252 | ND | 219 | 40.9 |
| E | 7-23-85 | 29 | 1134 | 1200 | 483 | 719 | 865 | 992 | 855 | 544 | 2267 | 425 | 948 | 359.9 |
| F | 7-26-85 | 32 | 3798 | 910 | 1497 | 1542 | 1000 | 2060 | ND | 1313 | 835 | ND | 1619 | 654.8 |
| E | 7-30-85 | 36 | 1933 | 1079 | 1592 | 570 | 1815 | 1091 | 593 | 1582 | 1966 | 807 | 1303 | 474.8 |
| F | 8-02-85 | 39 | 2050 | 664 | 619 | 1080 | 396 | 457 | ND | 416 | 656 | ND | 792 | 467.6 |
| F | 8-09-85 | 46 | 1385 | 975 | 1221 | 1786 | 416 | 1478 | ND | 704 | 807 | ND | 1097 | 516.1 |
| F | 8-16-85 | 53 | 845 | 758 | 684 | 1031 | 501 | 859 | ND | 693 | 1073 | ND | 806 | 278.3 |
| F | 8-23-85 | 60 | 711 | 456 | 260 | 389 | 357 | 557 | ND | 324 | 731 | ND | 473 | 210.6 |
| F | 8-30-85 | 67 | 223 | 351 | 332 | 347 | 194 | 353 | ND | 264 | 524 | ND | 324 | 122.6 |
| F | 9-06-85 | 74 | 380 | 272 | 276 | 299 | 222 | 360 | ND | 287 | 312 | ND | 301 | 90.0 |
| F | 9-13-85 | 81 | 266 | 229 | 194 | 201 | 242 | 241 | ND | 188 | 223 | ND | 223 | 61.8 |
| F | 9-20-85 | 88 | 186 | 156 | 139 | 163 | 160 | 176 | ND | 163 | 253 | ND | 175 | 53.2 |
| F | 9-27-85 | 95 | 204 | 247 | 160 | 161 | 142 | 161 | ND | 136 | 176 | ND | 173 | 56.0 |
| F | 10-04-85 | 102 | 115 | 82 | 81 | 141 | 102 | 107 | ND | 77 | 100 | ND | 101 | 32.8 |
| F | 10-11-85 | 109 | 135 | 88 | 62 | 62 | 79 | 62 | ND | 62 | 64 | ND | 77 | 29.8 |

[a] Serum samples were analyzed at Research Triangle Institute using radioimmunoassay.
[b] ND = Not determined.

TABLE 4

CONTROL GROUPS FOR PHARMACOKINETICS STUDIES, PLACEBO MICROCAPSULES PREPARED WITH 85:15 DL-PLG: COMPOSITE D196-105-1S

| Group | Serum collection date | Day | Rat 1 | Rat 2 | Rat 3 | Rat 4 | Rat 5 | Rat 6 | Rat 7 | Rat 8 | Rat 9 | Rat 10 | Average LHRN in serum, pg/mL ± SE | |
|---|---|---|---|---|---|---|---|---|---|---|---|---|---|---|
| G | 6-24-85 | 0 | 100 | 100 | 116 | 137 | 596 | 120 | 99 | 145 | 99 | 104 | 162 | 81.3 |
| H | 6-24-85 | 0 | 100 | 100 | 99 | 99 | 100 | 100 | 100 | 100 | 99 | 100 | 100 | 0.5 |
| G | 7-02-85 | 9 | 100 | 100 | 100 | 100 | 100 | 100 | 100 | 100 | 100 | 100 | 100 | 0.1 |
| H | 7-05-85 | 11 | 82 | 82 | 82 | 82 | 82 | 82 | 82 | 82 | 82 | 82 | 82 | 0.1 |
| G | 7-09-85 | 15 | 100 | 100 | 100 | 100 | 100 | 100 | 100 | 100 | 100 | 100 | 100 | 0.1 |
| H | 7-12-85 | 18 | 83 | 82 | 82 | 91 | 94 | 82 | 82 | 88 | 82 | 82 | 85 | 3.6 |
| G | 7-16-85 | 22 | 96 | 96 | 96 | 96 | 96 | 96 | 96 | 96 | 96 | 96 | 96 | 0.1 |
| H | 7-19-85 | 25 | 96 | 96 | 96 | 96 | 96 | 96 | 96 | 96 | 96 | 96 | 96 | 0.1 |
| G | 7-23-85 | 29 | 96 | 96 | 96 | 96 | 96 | 96 | 96 | 96 | 96 | 96 | 96 | 0.1 |
| H | 7-26-85 | 32 | 99 | 99 | 99 | 99 | 99 | 99 | 99 | 99 | 99 | 99 | 99 | 0.1 |
| G | 7-30-85 | 36 | 99 | 99 | 99 | 99 | 99 | 99 | 99 | 99 | 99 | 99 | 99 | 0.1 |
| H | 8-02-85 | 39 | 70 | 73 | 74 | 146 | 73 | 62 | 57 | 75 | 71 | 63 | 78 | 14.7 |
| H | 8-09-85 | 46 | 68 | 74 | 80 | 150 | 87 | 63 | 57 | 58 | 71 | 69 | 78 | 16.0 |
| H | 8-16-85 | 53 | 108 | 24 | 24 | 48 | 24 | 24 | 24 | 41 | 24 | 24 | 37 | 16.3 |
| H | 8-23-85 | 60 | 39 | 43 | 54 | 104 | 49 | 39 | 38 | 54 | 66 | 37 | 52 | 12.3 |
| H | 8-30-85 | 67 | 64 | 43 | 63 | 160 | 84 | 72 | 53 | 53 | 76 | 64 | 73 | 19.2 |
| H | 9-06-85 | 74 | 66 | 86 | 71 | 126 | 78 | 77 | 56 | 78 | 90 | 74 | 80 | 11.7 |
| H | 9-13-85 | 81 | 108 | 93 | 121 | 129 | 105 | 163 | 81 | 112 | 116 | 93 | 112 | 14.3 |
| H | 9-20-85 | 88 | 70 | 73 | 77 | 132 | 94 | 88 | 70 | 65 | 85 | 97 | 85 | 13.0 |
| H | 9-27-85 | 95 | 98 | 97 | 94 | 85 | 85 | 82 | 105 | 95 | 104 | 79 | 92 | 6.5 |
| H | 10-04-85 | 102 | 63 | 62 | 77 | 85 | 65 | 70 | 62 | 62 | 66 | 73 | 69 | 6.2 |
| H | 10-11-85 | 109 | 64 | 62 | 62 | 62 | 62 | 62 | 62 | 62 | 65 | 62 | 63 | 0.8 |
| H | 10-18-85 | 116 | 62 | 62 | 62 | 68 | 62 | 62 | 55 | 55 | 57 | 64 | 61 | 3.1 |
| H | 10-25-85 | 123 | 58 | 62 | 56 | 85 | 67 | 57 | 55 | 61 | 55 | 67 | 62 | 6.4 |
| H | 11-01-85 | 130 | 85 | 56 | 73 | 97 | 72 | 80 | 71 | 65 | 87 | 70 | 77 | 9.1 |
| H | 11-08-85 | 137 | 74 | 63 | 87 | 75 | 83 | 71 | 55 | 66 | 73 | 60 | 71 | 7.8 |
| H | 11-15-85 | 144 | 89 | 89 | 89 | 89 | 89 | 89 | 89 | 89 | 89 | 89 | 89 | 0.0 |
| H | 11-22-85 | 151 | 92 | 89 | 89 | 89 | 89 | 89 | 89 | 89 | 96 | 89 | 90 | 1.6 |

TABLE 4-continued

CONTROL GROUPS FOR PHARMACOKINETICS STUDIES, PLACEBO MICROCAPSULES
PREPARED WITH 85:15 DL-PLG: COMPOSITE D196-105-1S

| Group | Serum collection date | Day | Rat 1 | Rat 2 | Rat 3 | Rat 4 | Rat 5 | Rat 6 | Rat 7 | Rat 8 | Rat 9 | Rat 10 | Average LHRN in serum, pg/mL ± SE | |
|---|---|---|---|---|---|---|---|---|---|---|---|---|---|---|
| H | 11-29-85 | 158 | 89 | 89 | 89 | 89 | 89 | 89 | 89 | 89 | 89 | 89 | 89 | 0.0 |
| H | 12-06-85 | 164 | 89 | 89 | 89 | 93 | 89 | 89 | 89 | 89 | 89 | 89 | 89 | 0.7 |
| H | 12-13-85 | 171 | 102 | 102 | 102 | 102 | 102 | 102 | 102 | 102 | 103 | 102 | 102 | 0.2 |
| H | 12-20-85 | 178 | 102 | 103 | 102 | 102 | 102 | 102 | 102 | 102 | 102 | 102 | 102 | 0.2 |
| H | 12-27-85 | 185 | 102 | 102 | 102 | 102 | 102 | 130 | 102 | 102 | 102 | 102 | 105 | 5.0 |
| H | 1-03-86 | 192 | 113 | 108 | 102 | 102 | 107 | 105 | 102 | 102 | 102 | 102 | 105 | 3.0 |

[a] Serum samples were analyzed at Research Triangle Institute using radioimmunoassay.

What we claim is:

1. A method of preparing a composition for delivering a an effective amount of a constant dose of an active ingredient to an animal over a preselected, prolonged period of time, comprising the steps of:
    (a) encapsulating effective amounts of said ingredient in first and second separate biodegradable and biocompatible copolymer excipients having different monomers ratios to form first and second microcapsules, each of said microcapsules having of a different rate of release therefrom of said ingredient; and
    (b) combining an effective amount of said first and second microcapsules to form said composition having a delivery profile wherein the release of said ingredient through said second microcapsule begins as the release of said ingredient through said first microcapsule declines.

2. A method as claimed in claim 1, further including the step of administering an effective amount of said composition to the animal.

3. A method as claimed in claim 1, wherein said excipient is selected from the group consisting of polyacetal polymers, polyorthoesters, polyesteramides, polycaprolactone and copolymers thereof, polycarbonates, polyhydroxybuterate and copolymers thereof, polymaleamides, copolyaxalates, and polysaccharides.

4. The method as claimed in claim 1, wherein a copolymer excipient is poly(D,L-lactide-co-glycolide).

5. The method as claimed in claim 5, wherein the copolymer excipients have mole ratios of lactide to glycolide of 40:60 to 85:15, respectively.

6. The method as claimed in claim 1, wherein said active ingredient is a bioactive molecule.

7. The method as claimed in claim 1, wherein said active ingredient is a peptide.

8. The method of claim 7, wherein said peptide is hormonally active.

9. The method as claimed in claim 7, wherein said peptide is a luteinizing hormone releasing hormone or an analogue thereof.

10. The method of claim 1, wherein said active ingredient is a protein.

11. The method as claimed in claim 7, wherein said peptide is [D-Trp$^6$, des-Gly$^{10}$]-LHRH ethylamide.

12. The method as claimed in claim 1, wherein said first microcapsule comprises 3 percent by weight loaded [D-Trp$^6$, des-Gly$^{10}$]-LHRH ethylamide encapsulated in a copolymer excipient having a mole ratio of 52 percent lactide to 48 percent glycolide and wherein said second microcapsule comprises 10 percent by weight loaded [D-Trp$^6$, des-Gly$^{10}$]-LHRH ethylamide encapsulated in a copolymer excipient having a mole ratio of 68 percent lactide to 32 percent glycolide.

13. The method as claimed in claim 12, wherein said combining step further comprises adding to said composition an effective amount of 8 percent by weight loaded [D-Trp$^6$, des-Gly$^{10}$]-LHRH ethylamide encapsulated in a copolymer excipient having a mole ratio of 85 percent lactide to 15 percent glycolide.

14. The method as claimed in claim 13, wherein [D-Trp$^6$, des-Gly$^{10}$]-LHRH ethylamide is delivered at a constant rate ranging from 50 μg to 250 μg per day for approximately 180 days.

15. The method as claimed in claim 7, wherein said peptide is [D-N-Ac-4-Cl-Phe$^2$, D-Trp$^6$, D-Ala$^{10}$]-LHRH.

16. The method as claimed in claim 15, wherein said [D-N-Ac-4-Cl-Phe$^2$, D-Trp$^6$, D-Ala$^{10}$]-LHRH is delivered at a constant rate of about 200 μg to 500 μg per day for at least 90 days.

17. The method as claimed in claim 1, wherein said administering step is parenterally.

18. The method as claimed in claim 1, wherein said administering step is intramuscularly.

19. A composition capable of delivering an effective amount of a constant dose of an active ingredient to an animal over a preselected, prolonged period of time, comprising a blend of effective amounts of an active ingredient encapsulated in at least two biodegradable and biocompatible copolymer excipients having different monomers ratios to form first and second microcapsules, each excipient having of a different rate of release of said ingredient therethrough, said composition having a delivery profile wherein the release of said ingredient through said second microcapsule begins as the release of said ingredient through said first microcapsule declines.

20. A composition as claimed in claim 19, wherein said copolymer excipients are poly(D,L-lactide-co-glycolide).

21. A composition as claimed in claim 20, wherein said copolymer excipients have mole ratios of lactide to glycolide of 40:60 to 85:15 respectively.

22. A composition as claimed in claim 19, wherein said active ingredient is a bioactive molecule.

23. A composition as claimed in claim 19, wherein said active ingredient is a peptide.

24. A composition as claimed in claim 23, wherein said peptide is hormonally active.

25. A composition as claimed in claim 23, wherein said peptide is a luteinizing hormone releasing hormone or an analog thereof.

26. A composition as claimed in claim 25, wherein said luteinizing hormone releasing hormone is [D-Trp$^6$, des-Gly$^{10}$]-LHRH ethylamide.

27. A composition as claimed in claim 19, wherein said active ingredient is a protein.

28. A composition as claimed in claim 19, wherein said blend of microencapsulated peptide is comprised of appropriate amounts of 3% by weight loaded [D-Trp$^6$, des-Gly$^{10}$]-LHRH ethylamide encapsulated in a copolymer excipient having a mole ratio of 52% lactide to 48% glycolide, and 10% by weight loaded [D-Trp$^6$, des-Gly$^{10}$]-LHRH ethylamide encapsulated in a copolymer excipient having a mole ratio of 68% lactide to 32% glycolide.

29. A composition as claimed in claim 28 and further comprising an appropriate amount of 8% by weight loaded [D-Trp$^6$, des-Gly$^{10}$]-LHRH ethylamide encapsulated in a copolymer excipient having a mole ratio of 85% lactide to 15% glycolide added to said blend.

30. A composition as claimed in claim 29, wherein said blend delivers [D-Trp$^6$, des-Gly$^{10}$]-LHRH ethylamide at a constant rate of about 50 µg to 250 µg per day for 180 days.

31. A composition as claimed in claim 23, wherein said peptide is [D-N-Ac-4-Cl-Phe$^2$, D-Trp$^6$, D-Ala$^{10}$]-LHRH.

32. A composition as claimed in claim 31, wherein said blend delivers [D-N-Ac-4-Cl-Phe$^2$, D-Trp$^6$, D-Ala$^{10}$]-LHRH at a constant rate of about 200 µg to 500 µg per day for at least 90 days.

* * * * *

UNITED STATES PATENT AND TRADEMARK OFFICE
CERTIFICATE OF CORRECTION

PATENT NO. : 4,897,268
DATED : January 30, 1990
INVENTOR(S) : Thomas R. Tice and Richard M. Gilley It is certified that error appears in the above-identified patent and that said Letters Patent is hereby corrected as shown below:

In Claim 17, line 32, delete "1" and substitute -- 2 --.

In Claim 18, line 34, delete "1" and substitute -- 2 --.

Signed and Sealed this

Twenty-sixth Day of February, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,897,268

DATED : January 30, 1990

INVENTOR(S) : Thomas R. Tice and Richard M. Gilley

It is certified that error appears in the above-identified patent and that said Letters Patent is hereby corrected as shown below:

COLUMN 12

In Claim 17, line 32, delete "1" and substitute -- 2 --.

In Claim 18, line 34, delete "1" and substitute -- 2 --.

In Column 1 at line 4 insert the following:

--FEDERALLY SPONSORED RESEARCH

This invention was made in the course of Grant N01-HD-3-2824 awarded by the National Institute of Child Health and Development of the National Institutes of Health and, therefore, the Government has rights in this invention.--

Signed and Sealed this

Third Day of September, 1991

Attest:

HARRY F. MANBECK, JR.

Attesting Officer

Commissioner of Patents and Trademarks